United States Patent [19]

Shibata

[11] Patent Number: 4,642,174
[45] Date of Patent: Feb. 10, 1987

[54] APPARATUS FOR DETERMINING THE OXYGEN CONTENT IN GASES

[75] Inventor: Masahiro Shibata, Aichi, Japan

[73] Assignee: Nippondenso Co., Ltd., Kariya, Japan

[21] Appl. No.: 751,729

[22] Filed: Jul. 3, 1985

[30] Foreign Application Priority Data

Jul. 6, 1984 [JP] Japan .................. 59-140016

[51] Int. Cl.[4] .................................... G01N 27/56
[52] U.S. Cl. .................... 204/408; 204/424; 204/425; 204/428; 204/429
[58] Field of Search ............. 204/408, 421, 424, 425, 204/426, 427, 428, 429

[56] References Cited

U.S. PATENT DOCUMENTS

| | | | |
|---|---|---|---|
| 4,040,930 | 8/1977 | Dillon | 204/429 |
| 4,111,778 | 9/1978 | Davis et al. | 204/428 |
| 4,145,272 | 3/1979 | Nakamura et al. | 204/428 X |
| 4,152,232 | 5/1979 | Otsuka et al. | 204/428 X |
| 4,157,282 | 5/1979 | Riddel | 204/428 X |
| 4,225,634 | 9/1980 | Tanaka et al. | 204/429 X |
| 4,264,425 | 4/1981 | Kimura et al. | 204/429 X |
| 4,282,080 | 8/1981 | Muller et al. | 204/426 |
| 4,402,820 | 9/1983 | Sano et al. | 204/429 X |
| 4,437,971 | 3/1984 | Csanitz et al. | 204/428 X |
| 4,476,008 | 10/1984 | Sano et al. | 204/429 X |
| 4,512,871 | 4/1985 | Kato et al. | 204/429 |

FOREIGN PATENT DOCUMENTS 55-116248  9/1980  Japan .
57-92159   6/1982  Japan .
57-166554 10/1982  Japan .

*Primary Examiner*—John F. Niebling
*Assistant Examiner*—Nam X. Nguyen
*Attorney, Agent, or Firm*—Cushman, Darby & Cushman

[57] ABSTRACT

An apparatus for determining oxygen concentration in exhaust gases from an automotive engine is provided which includes a solid electrolytic member of oxygen ion conductive material disposed between a pair of first and second electrodes. In this apparatus, a porous insulating layer is formed on a cylindrical heater made of ceramics and a first electrode is formed on the outer periphery of the porous insulating layer. A solid electrolytic member is formed as a thin film form on the outer periphery of the first electrode layer and a second electrode is formed on the outer periphery of the solid electrolytic film member. Since the solid electrolytic film is formed such that it overlies the outer periphery of the cylindrical heater, it has an adequate structural strength even if formed to be a thinner film.

10 Claims, 9 Drawing Figures

F I G. 6A
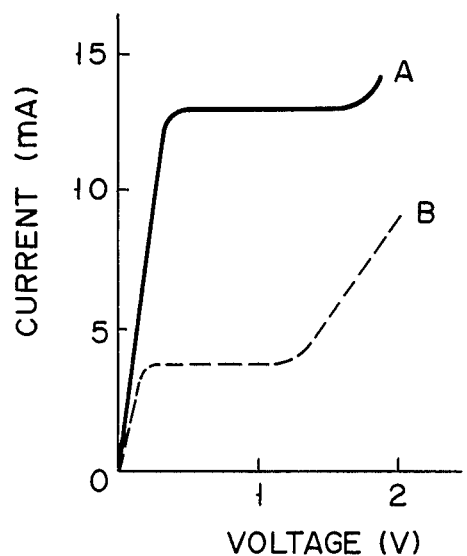
F I G. 6B
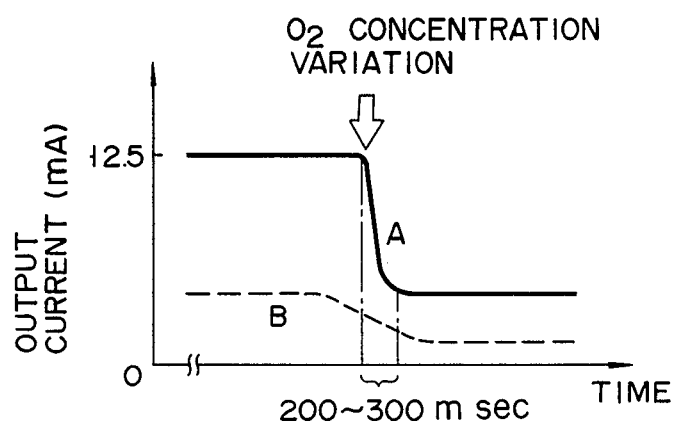

APPARATUS FOR DETERMINING THE OXYGEN CONTENT IN GASES

BACKGROUND OF THE INVENTION

This invention relates to an apparatus for determining the oxygen content in gases and, in particular, to an apparatus used in an automotive engine mechanism and measuring a saturated current level which corresponds to the oxygen concentration in the exhaust gas from the engine, for an electronic control of the engine.

An apparatus for determining the oxygen concentration in gases by measuring a saturated current level is well known in U.S. Pat. No. 4,282,080; Japanese Patent Disclosure (KOKAI) No. 55-116248; Japanese Patent Disclosure (KOKAI) No. 57-166554 and Japanese Utility Model Disclosure (KOKAI) No. 57-92159.

An oxygen concentration detecting element of the oxygen content determining apparatus includes a plate-like, solid electrolytic member made of oxygen ion conductive metal oxide and a pair of electrodes attached one at each side of the electrolytic member.

When a voltage is applied between the pair of electrodes, oxygen in an atmosphere to be measured is migrated as ions in the solid electrolytic member from one electrode toward the other for diffusion.

The voltage-current characteristic with respect to the above electrode pair exhibits a constant current characteristic within a certain voltage range. Hereinafter, a current corresponding to such a voltage range of the constant current characteristic is referred to as a saturated current level.

The saturated current level corresponds to the amount of oxygen ions diffusing in the solid electrolytic member. Thus it is possible to know the oxygen concentration in gases to be measured, by applying such a voltage between the pair of electrodes that the current is at a saturated current level, and measuring the saturated current level at that time.

The oxygen content determining apparatus is mounted on an automotive exhaust pipe in order to determine the oxygen concentration in the exhaust gases. In this case it is required that the solid electrolytic member has an enough structural strength to withstand severe conditions, such as intense vibrations, to which it is subjected when incorporated into an automotive vehicle.

Conventionally in oxygen content determining apparatus of such a type, the solid electrolytic member is formed of a plate-like or a cup-like sintered ceramics, and a pair of electrodes are formed at the surfaces of the member. The solid electrolytic member shows a withstand characteristic against the above-mentioned severe conditions, only when it is formed to a thick shape.

It is preferred that the solid electrolytic member be formed with a thin shape, because the thinner member provides a smaller internal resistance and permits the temperature for operating the detecting element to be lower. It is difficult, however, to form the thin solid electrolytic member from the standpoint of securing the above-mentioned adequate structural strength. It is therefore necessary to set the operating temperature for detection of oxygen concentration at a high level, for example, above 700° C. As a result, it is necessary to enhance the capacity of the heater. This results in complicating the structure and increasing power consumption of the heater.

SUMMARY OF THE INVENTION

It is accordingly one object of this invention to provide an apparatus for determining the oxygen content under the electronic control of an automotive engine by measuring a saturated current level which corresponds to the oxygen concentration in exhaust gases from the engine, while maintaining a sufficient structural strength for the solid electrolytic member of the oxygen concentration detecting element regardless of a small thickness of the electrolytic member.

Another object of this invention is to provide an apparatus which can lower a temperature at which it is operated.

Another object of this invention is to provide an apparatus which can simplify the structure of a heater and thus assuring the ready manufacture of the heater.

Further objects and advantages of this invention can be seen in the following description.

An oxygen content determining apparatus according to this invention comprises a bar shaped ceramics heater, a porous insulating layer formed on the outer periphery of the ceramics heater, a first electrode formed on the outer periphery of the porous insulating layer, a solid electrolytic film formed on a part of the outer periphery of the first electrode, a second electrode formed on the outer periphery of the solid electrolytic film in a manner insulated from the first electrode by an insulating layer, and an oxygen diffusion resistant layer formed on the outer periphery of the second electrode. The apparatus is mounted in an automotive engine mechanism, with an area incorporating the solid electrolytic film being exposed to the exhaust gases from the automotive engine. The oxygen concentration can be detected by applying a given voltage between the first and second electrodes and measuring the level of a current.

In the apparatus according to this invention, since the solid electrolytic film is formed on the outer periphery of the cylindrical ceramic heater via the porous insulating layer, it assures an adequate structural strength, even if it is thinner. In consequence, the internal resistance of the solid electrolytic film can be adequately decreased to permit improving the sensitivity of detection of the oxygen concentration and thus enhancing the response to the electronic control of the engine. It is also possible to effectively lower the operating temperature of the oxygen concentration detecting element. Furthermore, the heater can be made compact due to the provision of the adequately-thin, solid electrolytic film and thus the apparatus involving the detecting element and heater can also be made compact and assures a ready attachment to the engine mechanism. Since the solid electrolytic film is located substantially in direct contact with the surface of the heater, an enhanced heating efficiency of the heater is assured with respect to the solid electrolytic film, thus saving a power consumption of the heater and, in addition, positively improving the durability of the heater.

BRIEF DESCRIPTION OF THE DRAWINGS

FIGS. 6A and 6B are graphs showing the act of the porous insulating layer of the detecting element.

DETAILED DESCRIPTION OF THE PREFERRED EMBODIMENT

Figure 1:
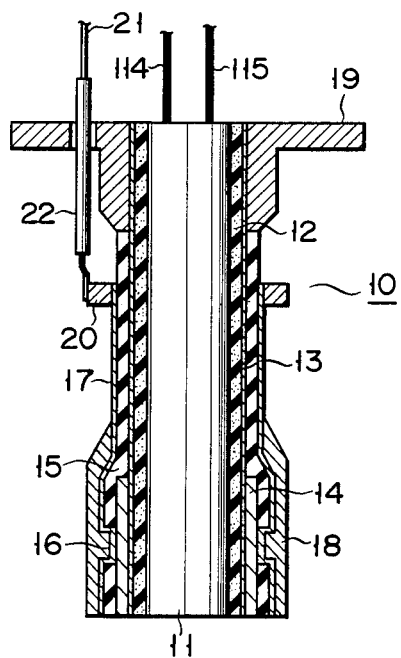
FIG. 1 is a cross-sectional view of an oxygen concentration detecting element in an apparatus according to one embodiment of this invention.

FIG. 1 shows an oxygen concentration detecting element 10 which composes a part of an apparatus according to this invention. The oxygen concentration detecting element 10 has a cylindrical heater 11 made of ceramics.

Figure 2A:
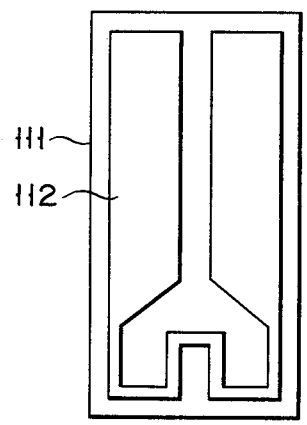
FIGS. 2A to 2C are views for explaining a ceramic heater of the oxygen concentration detecting element.
Figures 2B, 2C:
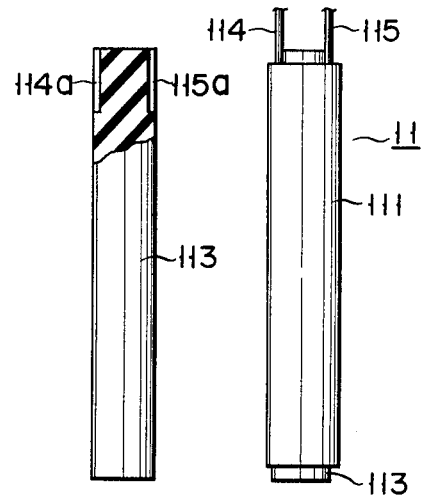

The ceramic heater 11 includes an unbaked alumina sheet 111 shown in FIG. 2A. As shown in this figure, the paste of heat-resistant metal, such as Pt, is screen-printed on the surface of the alumina sheet 111 to provide a heater pattern 112. The alumina sheet 111 having the heater pattern 112 is wrapped on the outer periphery of a core rod 113 of unbaked alumina, as shown in FIG. 2C, with the pattern-printed surface inside. The resultant structure is baked integrally to provide a ceramic heater 11.

A pair of grooves 114a, 115a are formed on the outer periphery of the proximal end of the core rod 113 as shown in FIG. 2B. Into the grooves 114a, 115a, a pair of leads 114, 115 are fitted as shown in FIG. 2C and brazed there. Then the pattern-printed alumina sheet 111 is wrapped on the outer periphery of the core rod 113, having the leads 114, 115, with the result that the leads 114, 115 for the heater pattern 112 extend outward.

As shown in FIG. 1, a porous insulating layer 12 made of insulating metal oxide and having a thickness of 100 to 200 $\mu$m is formed on the outer periphery of the cylindrical ceramic heater 11. The porosity of insulating layer 12 is 4 to 20% in order that oxygen which is drawn in from a gas atmosphere to be measured can pass therethrough. The porous insulating layer 12 may be formed on the surface of the heater 11 by plasma flame spraying with powder of an electrically insulating material, such as alumina ($Al_2O_3$) or magnesia-alumina ($MgO$-$Al_2O_3$) spinel, having a particle size of 50 to 100 $\mu$m.

A first electrode 13 of Pt which is used as positive electrode is formed by a chemically plating method on the outer periphery of the porous insulating layer 12. The electrode 13 is a porous thin film to permit the gas to freely pass therethrough.

A solid electrolytic film 14 is formed on the outer periphery of the distal end of the first electrode 13 and is a dense film of about 100 $\mu$m in thickness. The film 14 is deposited on the surface of the first electrode 13 by following process; material consisting of 90-95 mole % of $ZrO_2$ and 5-10 mole % of $Y_2O_3$ is mixed, crushed, granulated and preheated yielding powder having a particle size of $1 \sim 20$ $\mu$m, and then the resultant powder is plasma frame sprayed at a high energy level of over 50 kw.

An insulating layer 15 is formed on the surface of the resultant structure. The insulating layer is made of, for example, $MgO$-$Al_2O_3$ spinel and has a thickness of about 50 $\mu$m. In more detail, the insulating layer 15 is formed on the surface of the electrode 13 such that it partly or never, covers the surface of the solid electrolytic film 14. FIG. 1 shows the former case where the insulating film 15 covers a part of the surface of the solid electrolytic film 14, noting that an area of the solid electrolytic film 14 which is not covered by the insulating film 15 serves as an oxygen concentration detecting area 16. The insulating layer 15 terminates short of the proximal end (upper end) of the electrode 13.

A second electrode 17, the negative electrode, is formed on the surface of the resultant structure including the surface of detecting area 16. The electrode 17 is porous to permit oxygen to pass therethrough. The electrode 17 can be formed by the chemical plating method as in the case of the electrodes 13, and it may terminate short of the insulating layer 15 as shown in FIG. 1.

An oxygen diffusion resistant layer 18 is formed on the surface of the outer periphery of the second electrode 17. The layer 18 has a thickness of 200 to 600 $\mu$m and a porosity of 3 to 8%, and is formed by virtue of plasma flame spraying with a chemically and thermally stable material, such as the $MgO$-$Al_2O_3$ spinel. The body of the oxygen concentration detecting element 10 is formed as set out above.

In the selection of the materials for these films or layers of the body of the detecting element 10 it is better that the porous insulating layer 12 consists of a material whose thermal expansion coefficient is within a range between the thermal expansion coefficient of the material for the solid electrolytic film 14 and that of the material for the sheet 111 of the ceramic heater 11, because a separation and fall of the solid electrolytic film 14 from the adjacent film or layer is prevented. For example, when the sheet 111 is made of $Al_2O_3$ with a thermal expansion coefficient of $8.5 \times 10^{-6}/°C$. and the solid electrolytic film 14 is made of full stabilized $ZrO_2$-$Y_2O_3$ with a thermal expansion coefficient of $10.5 \times 10^{-6}/°C$., then $ZrO_2$-$Y_2O_3$-$Al_2O_3$ with a thermal expansion coefficient of $9.5 \times 10^{-6}/°C$. is preferably selected as the material of the porous insulating layer 12. Further, in this combination, the insulating layer 15 preferably consists of $MgO$-$Al_2O_3$, having a thermal expansion coefficient of $8.5 \times 10^{-6}/°C$. and a thickness of about 50 $\mu$m, and the oxygen diffusion resistant layer 18 is made preferably of $ZrO_2$-$Y_2O_3$-$Al_2O_3$ with a thermal expansion coefficient of $10 \times 10^{-6}/°C$.

As shown in FIG. 1, a metal stem 19 is brazed to that proximal end of the body of the detecting element 10. The stem 19 is fitted over the outer periphery of the first electrode 13 and acts as an outer connection terminal of the electrode 13.

A metal ring 20 which acts as an outer connection terminal of the second electrode 17 is fitted over the outer periphery of the electrode 17. The ring 20 is connected to a lead 21, which extends up through the stem 19, as shown in FIG. 1, in a manner protected by an insulator 22.

In this way, the oxygen concentration detecting element 10 is provided which has the leads 114, 115 for the heater 11, the outer connection terminal (stem 19) for the first electrode 13, and the outer connection lead 21 for the second electrode 17.

Figure 3:
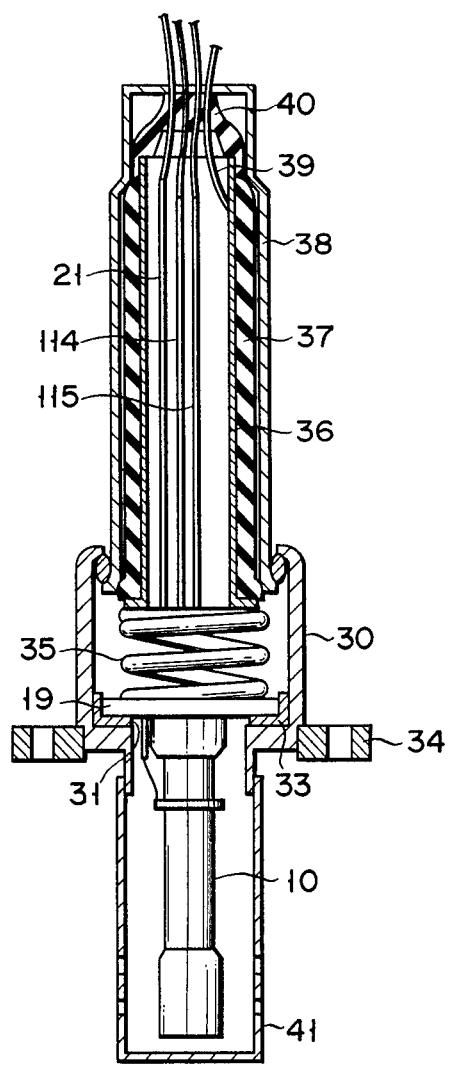
FIG. 3 is a cross-sectional view of the apparatus equipped with the detecting element shown in FIG. 1.

FIG. 3 shows an oxygen content determining apparatus incorporating the oxygen concentration detecting element 10 therein. Within a cylindrical housing 30 the stem 19 overlies a stepped section 31 of the housing 30 with a ceramics insulating plate 33 therebetween. The housing 30 has a metal flange 34 integrally which serves as a part for attaching the housing to an exhaust pipe of an engine not shown.

A spring 35 which pushes the stem 19 of the detecting element 10 against the stepped section 31 is set in the housing 30. The spring 35 is compressed by a metal pipe 36 with the result that the spring 35 and pipe 36 are electrically connected to the stem 19 of the detecting element 10. Thus spring 35 provides the outer connection terminal of the first electrode 13.

An insulating pipe 37 made of ceramics, such as alumina, is fitted over the outer periphery of the metal pipe 36 to provide an integral structure. The insulating pipe 37 is located within an outer protection tube 38 which is jointed to the housing 30 by caulking and thus the detecting element 10 is fixedly jointed to the housing 30 at a position where the stem 19 is located. In this case, the leads 21, 114 and 115 are brought to the outside through the metal pipe 36, and the lead 39 is welded to the metal pipe 36 which is connected to the electrode 13. The leads 21, 114, 115 and 39 are held in place by a rubber packing 40 which is attached to the metal pipe 36. The portions of these leads which extend out of the metal pipe 36 are used as assemblies to be connected to outer connectors.

The detecting element 10, except for the stem 19, extends beyond the housing 30 to be surrounded with a cover 41 having a number of through holes at a location facing the detecting section 16. When the apparatus of this invention is attached to an engine's exhaust pipe by use of the flange 34, the cover 41 is exposed to an inner space of the exhaust pipe and thus exhaust gas acts upon the oxygen concentration detecting element 10.

In the oxygen concentration detecting element 10 which is used as one element of the oxygen content determining apparatus, when voltage is applied across the first and second electrodes 13 and 17, a current flows from the electrode 13 into the electrode 17. This current is based on the following phenomenon: oxygen molecules which have passed through the oxygen diffusion resistant layer 18 are ionized to oxygen ions and these ions are migrated in the solid electrolytic film 14 made of oxygen ion conductive electrolytic material toward the first electrode 13. In the first electrode 13, the oxygen ions turn into oxygen molecules in accordance with the equation:

$$2O^{2-} - 4e^- \rightarrow O_2,$$

noting that the oxygen molecules thus generated are expelled toward the outside of the detecting element 10 through the porous insulating layer 12.

When the voltage between the electrodes 13 and 17 is sequentially increased, a voltage range exists in which range current does not increase because the passage of the oxygen molecules is restricted by the diffusion resistant layer 18. The level of a constant current present within the voltage range is referred to as a saturated current "Il" which is a signal for detecting oxygen concentration. Il is given by:

$$Il = (4FD_{O_2}/RT)S/l \cdot P_{O_2} \quad (1)$$

where
F: Farady constant
R: gas constant
$D_{O_2}$: diffusion coefficient of oxygen
T: absolute temperature
S: area of electrode
l: effective diffusion distance of the diffusion resistant layer
$P_{O_2}$: partial pressure of oxygen.

The saturated current level varies in accordance with the oxygen concentration of the gas to be measured. When a specific voltage is applied across the electrodes 13 and 17 and a saturated current level at that time is measured, then it is possible to know the oxygen concentration of the gas.

Figure 4:
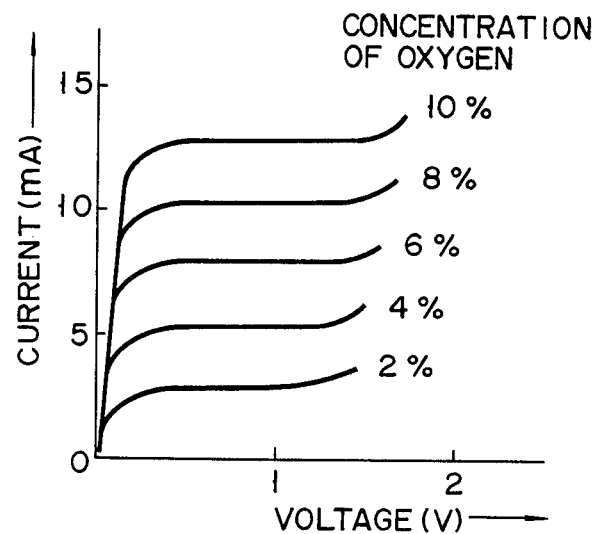
FIGS. 4 and 5 are graphs for explaining the operation characteristics of the detecting element.
Figure 5:
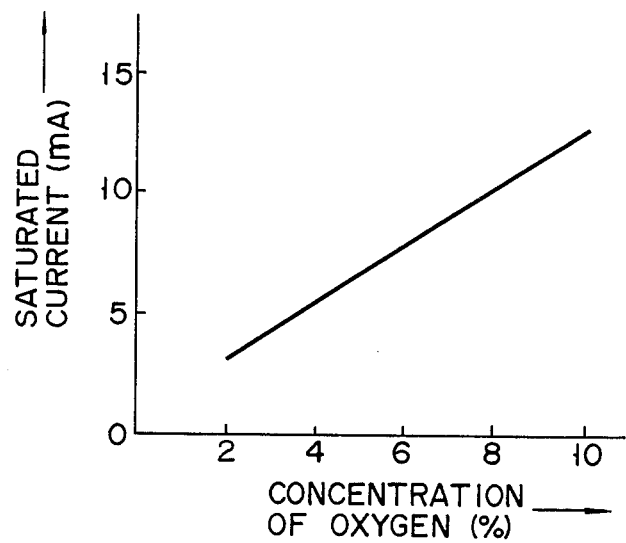

FIGS. 4 and 5 show the results of tests carried out on the oxygen concentration detecting element 10 in a model gas of $O_2$-$N_2$ at 600° C. As seen from FIG. 4, within a voltage range of about 0.4 V to 1.2 V the characteristic curves in the voltage-current became flat at the different level respectively according to each oxygen concentration, and the currents again increased with an increasing voltage.

Here, the constant current level involved is a saturated current level. The saturated current level varies based on Equation (1), depending upon the oxygen concentration.

FIG. 5 shows a relation between the oxygen concentration level and the saturated current level when a predetermined voltage of 0.7 V is applied. As seen from FIG. 5, the saturated current level varies in exact proportion to the oxygen concentration level. The air/fuel ratio of, for example, the automotive internal engine can be controlled by this current level. In practical application, since the temperature of the atmosphere gas varies and thus the saturated current level varies, the detection element is maintained at a constant temperature level by carrying current through the leads 114 and 115.

It is important to note that the porous insulating layer 12 plays an important part in the above-mentioned operation of the detecting element. As set out above, oxygen molecules are generated at the first electrode 13 due to a reaction of:

$$2O^{2-} - 4e^- \rightarrow O_2$$

The porous insulating layer 12 serves to expel the oxygen molecules toward the outside of the detecting element 10. Now suppose that there is no porous insulating layer 12 and thus the generated oxygen molecules are not smoothly expelled beyond the porous insulating layer 12. Then, an over voltage is generated, exerting an adverse influence over the diffusion rate of $O_2$ which is determined by the oxygen diffusion resistant layer 18. As a result, the detecting element without the porous insulating layer 12 shows a lower saturated current level than the detecting element with the porous insulating layer 12 under the same oxygen concentration, failing to provide any stable saturated current characteristic.

FIG. 6A shows such a state as mentioned, i.e., a result of measurements of the voltage-current characteristic of the detecting element (the curve A) with the porous insulating layer 12 and detecting element (the curve B) without the porous insulating layer 12. Here, the ordinate and abscissa in FIG. 6A are substantially the same as those of FIG. 4, noting that in FIG. 6A the measurements were conducted at the oxygen concentration of 10%. As seen from FIG. 6A, the current level of the curve B (the element without the porous insulating layer 12) is lower than that of the curve A and the saturated current characteristic of the curve B is not so stable as that of the curve A.

Furthermore, where no porous insulating layer 12 exists, a response of the detecting element to the variation of the oxygen concentration is lowered. FIG. 6B shows a time-sequential variation in the output currents of the detecting element (the curve A) with the porous insulating layer and the detecting element (the curve B) without the porous insulating layer when the oxygen concentration of a gas to be measured varies from 10% down to 3% at a voltage of 0.7 V. As seen from FIG. 6B, the curve A of the detecting element 10 with the porous insulating layer 12 shows a quick response to the $O_2$ concentration variation and thus an abrupt output drop, while the curve B of the detecting element without the porous insulating layer shows a slow response to the variation of oxygen concentration.

In each detecting element used in the above-mentioned experiments, the porous insulating layer (curve A only) has a porosity of 10% and a thickness of 100 μm, the oxygen diffusion resistant layer has a porosity of 6% and a thickness of 400 μm, the electrode is made of Pt, and the solid electrolytic film has a composition of $ZrO_2(90\%)$-$Y_2O_3(10\%)$ and a thickness of 100 μm.

In the oxygen concentration detecting element 10 of the above-mentioned embodiment the diffusion resistant layer 18 may be extended still farther than shown in FIG. 1 to serve as a protective layer for the second electrode 17. Further, the porous insulating layer 12 and insulating layer 15 may be formed not only by plasma frame spraying but also by other process, for example, by a dipping method. Furthermore, the first and second electrodes 13 and 17 can be formed by, for example, a chemical plating, electric plating, spattering and paste baking method.

Further, the solid electrolytic film 14 may be formed of not only the material as set out above but also, for example, $ZrO_2$-$YbO_3$-$CaO$, or the other oxygen ion conductive metal oxide.

What is claimed is:

1. An apparatus for determining the oxygen content in gases comprising:
   a bar-like ceramic heater having an outer surface;
   a porous first insulating layer which is formed on said outer surface of said ceramic heater by plasma flame spraying and permits the passage of oxygen molecules, said porous first insulating layer having an outer surface;
   a first electrode formed on said outer surface of said first insulating layer, said first electrode having an outer surface;
   a solid electrolyte film formed on said outer surface of said first electrode, said solid electrolyte film having an outer surface;
   a second electrode formed on said outer surface of said solid electrolyte film, said second electrode having an outer surface;
   a second insulating layer formed between said first and second electrodes to insulate said first and second electrodes from each other;
   an oxygen diffusion-resistant layer formed on said outer surface of said second electrode to permit oxygen molecules to migrate to said second electrode; and
   measuring means for applying a prescribed voltage between said first and second electrodes, and for measuring a current flowing therebetween in accordance with the application of said prescribed voltage.

2. An apparatus according to claim 1, in which said ceramic heater is cylindrical.

3. An apparatus according to claim 1, in which said porous first insulating layer has a porosity of 4 to 20%.

4. An apparatus according to claim 1, in which said porous first insulating layer has a thickness of 100 to 200 μm.

5. An apparatus according to claim 1, in which said oxygen diffusion resistant layer is porous to permit oxygen molecules to diffuse therein, and has a porosity of 3 to 8%.

6. An apparatus according to claim 1, in which said ceramic heater is made of $Al_2O_3$, said porous insulating layer is formed of one of $MgO$-$Al_2O_3$ and $Al_2O_3$, said solid electrolyte film is formed of stabilized $ZrO_2$-$Y_2O_3$ and said second insulating layer is formed of $MgO$-$Al_2O_3$ and has a thickness of 50 μm.

7. An apparatus according to claim 1, in which said solid electrolyte film is formed at the neighborhood of the distal end of said ceramic heater, said porous first insulating layer and said first electrode extend toward the proximal end of said heater, and a metal stem is fitted, as a fixing member, over the outer periphery of the proximal end of said first electrode and acts as the terminal of said first electrode.

8. An apparatus according to claim 7, in which said second electrode terminates short of said metal stem and in the neighborhood of that proximal end of said ceramic heater where said solid electrolyte film is therefore absent, a metal ring is fitted over the outer periphery of said second electrode so as to electrically contact with said second electrode, and a lead fixed to said second electrode extends through a flange of said metal stem in an insulative fashion and acts as a terminal of said second electrode.

9. An apparatus according to claim 1, in which said solid electrolyte film has a predetermined detecting area, said second insulating layer is formed on said outer surface of said first electrode only outside said predetermined detecting area, and said second electrode contacts said solid electrolyte film only within said predetermined detecting area.

10. An apparatus according to claim 1, in which said porous first insulating layer has a coefficient of thermal expansion which is intermediate that of said ceramic heater and that of said solid electrolyte film.

* * * * *